United States Patent [19]

Hu et al.

[11] Patent Number: 5,786,472
[45] Date of Patent: Jul. 28, 1998

[54] PROCESS FOR MAKING DIHYDROPYRIMIDINONES

[75] Inventors: Essa Hsinyi Hu, Edison; Daniel R. Sidler, Whitehouse Station; Ulf H. Dolling, Westfield, all of N.J.; Michael A. Patane, Harleysville, Pa.

[73] Assignee: Merck & Co., Inc., Rahway, N.J.

[21] Appl. No.: 766,400

[22] Filed: Dec. 12, 1996

Related U.S. Application Data

[60] Provisional application No. 60/008,641 Dec. 14, 1995.

[51] Int. Cl.[6] .................................................. C07D 239/36
[52] U.S. Cl. .................................................. 544/318
[58] Field of Search .................................. 544/315, 318

[56] References Cited

U.S. PATENT DOCUMENTS 4,675,321  6/1987  Baldwin et al. ..................... 544/318

*Primary Examiner*—John M. Ford
*Attorney, Agent, or Firm*—Melvin Winokur; Kenneth R. Walton

[57] ABSTRACT

The present invention provides a process for forming 5-(alkyl or alkoxy)carbonyl-6-alkyl-4-(aryl or alkyl)-3,4-2(1H)-dihydropyrimidinones by combining a β-keto ester or diketone, an aldehyde and urea in the presence of a boron reagent, a metal salt (e.g., $Cu_2O$) and a catalyst (e.g., acid). The reaction is typically run in one pot in a solvent to afford dihydropyrimidinones in higher yields and with easier work up than previously known methods.

24 Claims, No Drawings

PROCESS FOR MAKING DIHYDROPYRIMIDINONES

FIELD OF THE INVENTION

This application is related to U.S. Ser. No. 60/008,641, filed as a provisional application on Dec. 14, 1995, the contents of which are hereby incorporated by reference.

The present invention provides a process for forming 5-(alkyl or alkoxy)carbonyl-6-alkyl-4-(aryl or alkyl)-3,4-2 (1H)-dihydropyrimidinones by combining a β-keto ester or diketone, an aldehyde and urea. More particularly, the reaction is run in one pot in the presence of a boron reagent, a metal salt and a catalyst to afford yields much higher than from currently accepted methods.

BACKGROUND OF THE INVENTION

Dihydropyrimidinone compounds have been extensively studied as calcium channel blockers useful as antihypertensive agents. [See e.g., K. S. Atwal et al., *J. Med. Chem* 34, 806 (1991); K. S. Atwal et al., *J. Med. Chem* 33, 2629 (1990); H. Cho et al., *J. Med. Chem* 32, 2399 (1989); Baldwin et al., U.S. Pat. No. 4,675,321, issued Jun. 23, 1987]. More recently, a number of dihydropyrimidinones have been identified as alpha 1a antagonists useful for the treatment of benign prostatic hyperplasia (BPH). [See PCT International Patent Application publication no. WO 96/14846, published 23 May 1996]

The reaction of numerous aldehydes with urea and a β-keto ester to give a tetrahydropyrimidinone was discovered by [Biginelli, *Gazz. Chim. Ital.*, 23, 360 (1893)]. The Biginelli reaction has been studied, improved upon and a mechanism of formation of tetrahydropyrimidinone proposed. [K. Folkers and T. B. Johnson, *J. Am. Chem. Soc.*, 55, 3784 (1933); J. D. Fissekis, and F. Sweet, *J. Am. Chem. Soc.*, 95, 8741(1973)]. Thus in the past, the synthesis of dihydropyrimidinones was most often effected using β-keto ester, aryl aldehyde and urea following the principles of Folkers' method, i.e., catalytic amount of acid (e.g., HCl, $H_2SO_4$) in protic solvents (e.g., MeOH, EtOH, AcOH) and heating to reflux for a few hours. [K. Folkers and T. B. Johnson, supra]

There are, however, several disadvantages associated with using Folkers method. First, most of the yields were either around or below 50%. Second, HPLC assays often indicate that a substantial portion of the β-keto ester and aryl aldehyde starting materials are consumed to form alkylidene side product. Third, in cases where acetic acid is used as the solvent system, large amounts of aqueous bases are needed to work up the reaction and the use of sodium bicarbonate or sodium carbonate solutions result in violent bubbling.

More recently, alternative stepwise methods for making dihydropyrimidinones have been proposed (See e.g., K. S. Atwal and B. C. O'Reilly, *Heterocycles*, 26 (5), 1185 (1987); H. Cho et al., *J. Org. Chem.*, 50, 4227 (1985)]. However, these methods required several steps and the yields from these methods was still often relatively low.

Thus, a need remains for an improved method for making dihydropyrimidinones having reduced formation of unwanted side products resulting in higher yields and easier work-up.

It is therefore an object of the invention to identify an improved method for making dihydropyrimidinone compounds of formula (I).

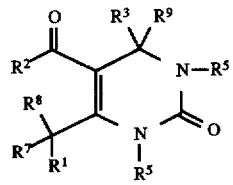

It is a further object of the invention to identify an improved method for making aryl-dihydropyrimidinone compounds of formula (III) which are useful as calcium channel blockers or as intermediates which can be further derivatized at the N-3 position (e.g., acylated as described in U.S. Pat. No. 4,675,321, or alkoxycarbonylated as described in Cho et al., *J. Med. Chem* 32, 2399 (1989)) to afford calcium channel blocking agents.

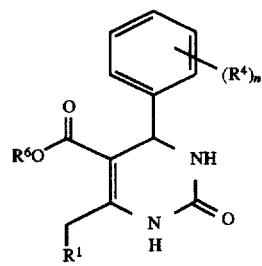

It is a further object of the invention to identify an improved method for making dihydropyrimidinone compounds of formulas (I) and (III) resulting in higher yields and easier work up than the previously known methods described above.

SUMMARY OF THE INVENTION

The present invention provides a method of forming a compound of formula I

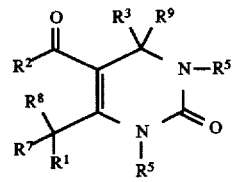

comprising reacting

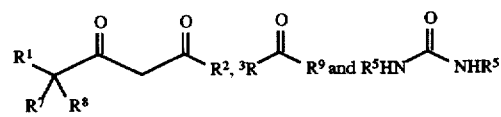

in the presence of a boron reagent, a metal salt and a catalyst to form the compound (I)

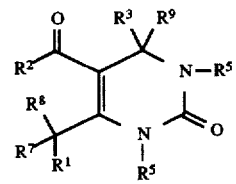

wherein $R^1$, $R^7$ and $R^8$ are each independently selected from hydrogen, halogen, halogenated $C_{1-10}$ alkyl, unsubsituted or substituted aryl, or unsubstituted or substituted $C_{1-10}$ alkyl wherein the substituent on the alkyl is selected from $C_{1-6}$ alkoxy, halogenated $C_{1-6}$ alkoxy or aryl;

$R^2$ is $C_{1-10}$ alkyl, $OR^6$, unsubstituted $C_{3-6}$ cycloalkyl or mono-, di- or tri-substituted $C_{3-6}$ cycloalkyl wherein the substitutents on the cycloalkyl are independently selected from hydroxy, $C_{1-6}$ alkyl, halogenated $C_{1-6}$ alkyl, $C_{1-6}$ alkoxy or halogenated $C_{1-6}$ alkoxy;

$R^3$ and $R^9$ are each independently selected from hydrogen, $C_{1-10}$ alkyl or

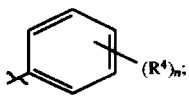

each $R^4$ is independently selected from hydrogen, halogen, cyano, $C_{1-6}$ alkoxy, halogenated $C_{1-6}$ alkoxy, nitro, $C_{1-10}$ alkyl or halogenated $C_{1-10}$ alkyl;

each $R^5$ is independently selected from hydrogen or $C_{1-10}$ alkyl;

$R^6$ is selected from unsubstituted or substituted $C_{1-10}$ alkyl wherein the substituent on the alkyl is selected from $C_{1-6}$ alkoxy, halogenated $C_{1-6}$ alkoxy or aryl; unsubstituted $C_{3-6}$ cycloalkyl or mono-, di- or tri-substituted $C_{3-6}$ cycloalkyl wherein the substitutents on the cycloalkyl are independently selected from hydroxy, $C_{1-6}$ alkyl, halogenated $C_{1-6}$ alkyl, $C_{1-6}$ alkoxy or halogenated $C_{1-6}$ alkoxy; or unsubstituted or substituted aryl; and n is an integer from one to five. Preferably, $R^9$ is hydrogen; more preferably, $R^7$, $R^8$ and $R^9$ are hydrogen and the compound I has the formula

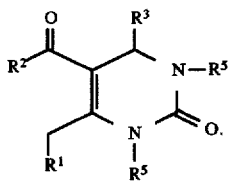

In one embodiment of the present invention is the method wherein
the metal salt is selected from copper (I) chloride, copper (I) oxide, copper (II) chloride, copper (II) sulfate, copper (II) acetate, nickel (II) bromide or palladium (II) acetate;
the catalyst is selected from acetic acid, trifluoroacetic acid, methanol, sulfuric acid, MsOH, dichloroacetic acid, HBr-PPh$_3$ or NH$_4$OAc;

$R^1$ is selected from hydrogen or $C_{1-8}$ alkyl;
$R^2$ is $C_{1-8}$ alkyl or $OR^6$;
$R^3$ is selected from $C_{1-8}$ alkyl or each $R^4$ is independently selected from hydrogen, halogen, $C_{1-5}$ alkoxy, nitro, $C_{1-8}$ alkyl or halogenated $C_{1-8}$ alkyl;
each $R^5$ is independently selected from hydrogen or $C_{1-8}$ alkyl;
$R^6$ is $C_{1-8}$ alkyl;
$R^7$, $R^8$ and $R^9$ are hydrogen; and
n is an integer from one to three.

In a class of the invention is the method further comprising the step of isolating the compound I In a subclass of the invention is the method comprising reacting in the presence of a boron reagent, a metal salt and a catalyst to form the compound (II)

wherein all variables are as defined above (i.e., each of the variables can be defined both as described in the broadest description of the general process and as described in the first embodiment of the present invention). Preferably, $R^9$ is hydrogen; more preferably, $R^7$, $R^8$ and $R^9$ are hydrogen and the compound II has the formula Illustrative of the invention is the method comprising reacting in the presence of a boron reagent, a metal salt and a catalyst to form the compound (III)

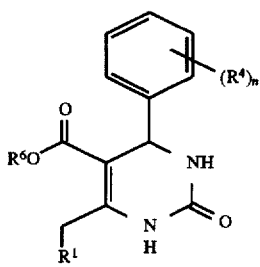

(III)

wherein all variables are as defined above (i.e., each of the variables can be defined both as described in the broadest description of the general process and as described in the first embodiment of the present invention).

Illustrating the invention is the method wherein the reaction is carried out in one pot.

An illustration of the invention is the method wherein the reaction is run in a solvent selected from an ether, an alcohol, a halogenated hydrocarbon or an acid. Preferably, the solvent is selected from tetrahydrofuran, methanol, methylene chloride or acetic acid. Most preferably, the solvent is tetrahydrofuran.

Exemplifying the invention is the method wherein the boron reagent is selected from $BF_3$, $BF_3 \cdot 2H_2O$, $BF_3 \cdot Me_2S$, $BF_3 \cdot HOAc$, $BF_3 \cdot Et2O$, $BF_3 \cdot Me_2O$, $BF_3 \cdot t\text{-BuOMe}$, $BF_3 \cdot CH_3OH$ or $BF_3 \cdot CH_3CH_2CH_2OH$. Preferably, the boron reagent is $BF_3 \cdot Et_2O$.

An example of the invention is the method wherein the metal salt is selected from copper (I) chloride, copper (I) oxide, copper (II) chloride, copper (II) sulfate, copper (II) acetate, nickel (II) bromide, palladium (II) acetate, copper bromide or palladium acetoacetate. Preferably, the metal salt is selected from copper (a) chloride, copper (I) oxide, copper (II) chloride, copper (II) sulfate, copper (II) acetate, nickel (II) bromide or palladium (II) acetate. More preferably, the metal salt is selected from copper (I) oxide, copper (I) chloride, nickel (II) bromide or palladium (II) acetate. Most preferably, the metal salt is copper (I) oxide.

Further illustrating the invention is the method wherein the catalyst is selected from acetic acid, trifluoroacetic acid, methanol, sulfuric acid, MsOH, dichloroacetic acid, $HBr \cdot PPh_3$, $NH_4OAc$, triethylamine, pyridine, cinchonine, quinine or quinidine. Preferably, the catalyst is selected from acetic acid, trifluoroacetic acid, methanol, sulfuric acid, MsOH, dichloroacetic acid, $HBr \cdot PPh_3$ or $NH_4OAc$. More preferably, the catalyst is selected from acetic acid, trifluoroacetic acid or methanol. Most preferably, the catalyst is acetic acid.

Further exemplifying the invention is the method wherein the metal salt is selected from copper (I) oxide, copper (I) chloride, nickel (II) bromide or palladium (II) acetate; the catalyst is selected from acetic acid, trifluoroacetic acid or methanol; and the solvent is selected from tetrahydrofuran, methanol or methylene chloride. Preferably, the metal salt is copper (I) oxide, the catalyst is acetic acid and the solvent is tetrahydrofuran. Most preferably, the metal salt is copper (I) oxide, the catalyst is acetic acid, the solvent is tetrahydrofuran and the reaction is carried out in one pot.

More particularly illustrating the invention is the method wherein the reaction is run at a temperature range of about 40° C. to 100° C. Preferably, the reaction is run at a temperature of about 65° C.

More specifically exemplifying the invention is the method wherein the reaction is heated for a period of from 1 to 20 hours, preferably, from 6 to 20 hours, most preferably, for about 18 hours.

Another aspect of the invention are the compounds of the formulas (IV) and (V), and salts thereof,

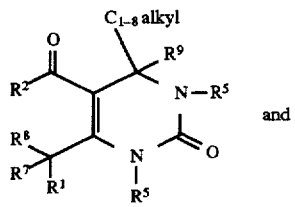

(IV)

and

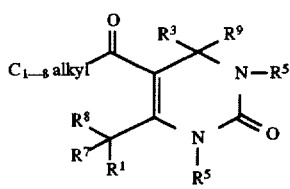

(V)

wherein $R^1$, $R^7$ and $R^8$ are each independently selected hydrogen, halogen, halogenated $C_{1-10}$ alkyl, unsubsituted or substituted aryl, or unsubstituted or substituted $C_{1-10}$ alkyl wherein the substituent on the alkyl is selected from $C_{1-6}$ alkoxy, halogenated $C_{1-6}$ alkoxy or aryl; $R^2$ is $C_{1-10}$ alkyl, $OR^6$, unsubstituted $C_{3-6}$ cycloalkyl or mono-, di- or trisubstituted $C_{3-6}$ cycloalkyl wherein the substitutents on the cycloalkyl are independently selected from hydroxy, $C_{1-6}$ alkyl, halogenated $C_{1-6}$ alkyl, $C_{1-6}$ alkoxy or halogenated $C_{1-6}$ alkoxy;

$R^3$ and $R^9$ are each independently selected from hydrogen, $C_{1-10}$ alkyl or

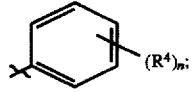

each $R^4$ is independently selected from hydrogen, halogen, cyano, $C_{1-6}$ alkoxy, halogenated $C_{1-6}$ alkoxy, nitro, $C_{1-10}$ alkyl or halogenated $C_{1-10}$ alkyl;

each $R^5$ is independently selected from hydrogen or $C_{1-10}$ alkyl;

$R^6$ is selected from unsubstituted or substituted $C_{1-10}$ alkyl wherein the substituent on the alkyl is selected from $C_{1-6}$ alkoxy, halogenated $C_{1-6}$ alkoxy or aryl; unsubstituted $C_{3-6}$ cycloalkyl or mono-, di- or trisubstituted $C_{3-6}$ cycloalkyl wherein the substitutents on the cycloalkyl are independently selected from hydroxy, $C_{1-6}$ alkyl, halogenated $C_{1-6}$ alkyl, $C_{1-6}$ alkoxy or halogenated $C_{1-6}$ alkoxy; or unsubstituted or substituted aryl; and n is an integer from one to five.

In one particular embodiment of this aspect of the invention, $R^1$ is selected from hydrogen or $C_{1-8}$ alkyl;

$R^2$ is selected from $C_{1-8}$ alkyl or $OR^6$, where $R^6$ is $C_{1-8}$ alkyl;

$R^3$ is selected from $C_{1-8}$ alkyl or

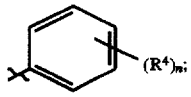

each $R^4$ is independently selected from hydrogen, halogen, cyano, $C_{1-5}$ alkoxy, nitro, $C_{1-8}$ alkyl or halogenated $C_{1-8}$ alkyl;

each $R^5$ is independently selected from hydrogen or $C_{1-8}$ alkyl;

$R^7$, $R^8$ and $R^9$ are hydrogen; and n is an integer of from one to three.

DETAILED DESCRIPTION OF THE INVENTION

The instant invention provides a process for preparing dihydropyrimidinones in high yields according to the following reaction scheme

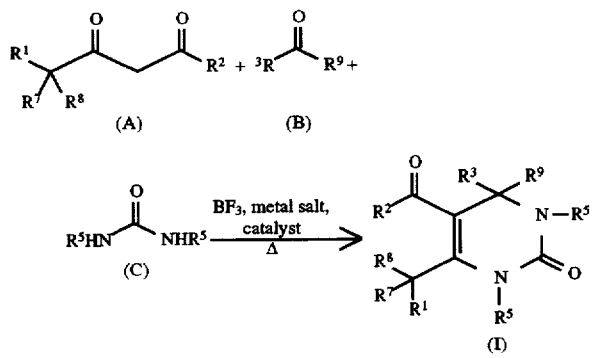

$R^1$, $R^7$ and $R^8$ are each independently selected from hydrogen, halogen, halogenated $C_{1-10}$ alkyl, unsubsituted or substituted aryl, or unsubstituted or substituted C-1 0 alkyl wherein the substituent on the alkyl is selected from $C_{1-6}$ alkoxy, halogenated $C_{1-6}$ alkoxy or aryl;

$R^2$ is $C_{1-10}$ alkyl, $OR^6$, unsubstituted $C_{3-6}$ cycloalkyl or mono-, di- or tri-substituted $C_{3-6}$ cycloalkyl wherein the substitutents on the cycloalkyl are independently selected from hydroxy, $C_{1-6}$ alkyl, halogenated $C_{1-6}$ alkyl, $C_{1-6}$ alkoxy or halogenated $C_{1-6}$ alkoxy;

$R^3$ and $R^9$ are each independently selected from hydrogen, $C_{1-10}$ alkyl or

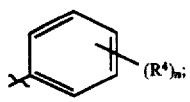

each $R^4$ is independently selected from hydrogen, halogen, cyano, $C_{1-6}$ alkoxy, halogenated $C_{1-6}$ alkoxy, nitro, $C_{1-10}$ alkyl or halogenated $C_{1-10}$ alkyl;

each $R^5$ is independently selected from hydrogen or $C_{1-10}$ alkyl;

$R^6$ is selected from unsubstituted or substituted $C_{1-10}$ alkyl wherein the substituent on the alkyl is selected from $C_{1-6}$ alkoxy, halogenated $C_{1-6}$ alkoxy or aryl; unsubstituted $C_{3-6}$ cycloalkyl or mono-, di- or tri-substituted $C_{3-6}$ cycloalkyl wherein the substitutents on the cycloalkyl are independently selected from hydroxy, $C_{1-6}$ alkyl, halogenated $C_{1-6}$ alkyl, $C_{1-6}$ alkoxy or halogenated $C_{1-6}$ alkoxy; or unsubstituted or substituted aryl; and n is an integer from one to five. Preferably, $R^7$, $R^8$ and $R^9$ are hydrogen and the compound I has the formula

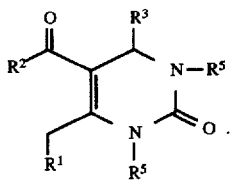

In a preferred embodiment of the instant invention is the improved process for forming 4-aryl-pyrimidinones of the formula (II) as shown below.

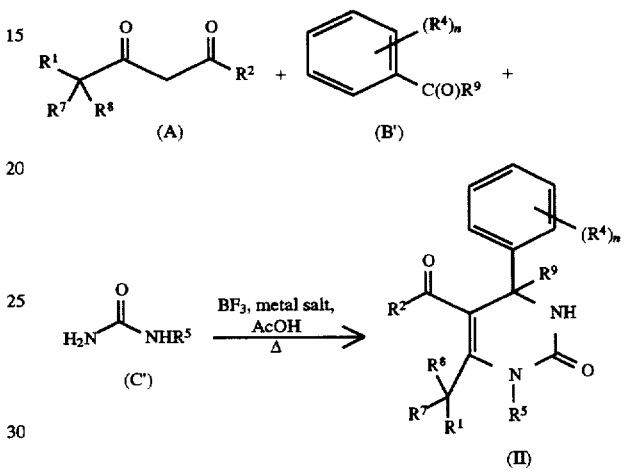

wherein $R^1$, $R^2$, $R^4$, $R^5$, $R^6$, $R^7$, $R^8$, $R^9$ and n are as defined above. Preferably, $R^7$, $R^8$ and $R^9$ are hydrogen and the compound II has the formula

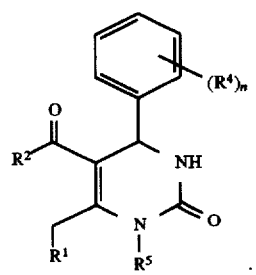

In the most preferred embodiment of the instant invention is the improved process for forming 4-aryl-pyrimidinones of the formula (III) as shown below.

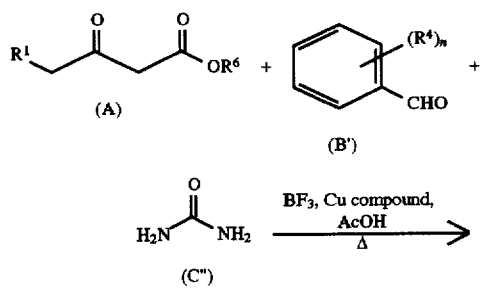

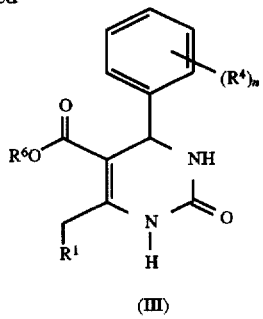

(III)

wherein $R^1$, $R^4$, $R^6$ and n are as defined above.

Compounds of formulas (I), (II) and (III) are useful as calcium channel blockers and as alpha 1a antagonists. More specifically, compounds of formula (III) are particularly preferred as calcium channel blockers, or as intermediates which can be further derivatized at the N-3 position (e.g., acylated as described in U.S. Pat. No. 4,675,321, or alkoxycarbonylated as described in Cho et al., *J. Med. Chem* 32, 2399 (1989)) to afford calcium channel blocking agents. Similarly, compounds of formula (III) are particularly preferred as alpha 1a antagonists, or as intermediates which can be further derivatized at the N-3 position as described in WO 96/14846, published 23 May 1996.

The reaction is run in one pot in a solvent selected from an oxygenated organic solvent (e.g., alcohol, ether), a halogenated hydrocarbon or an acid. Preferably, the solvent is selected from tetrahydrofuran, methanol, methylene chloride or acetic acid. Most preferably, the solvent is tetrahydrofuran.

A wide array of β-keto esters or diketones (A) and substituted-benzaldehydes (B') are commercially available allowing one to make aryl-dihydropyrimidinones having a large variety of substituents for $R^1$, $R^2$ and $R^3$. Moreover, in addition to aryl aldehydes, it is also possible to utilize alkyl aldehydes in the instant invention to afford alkyl-pyrimidinones of the formula (IV)

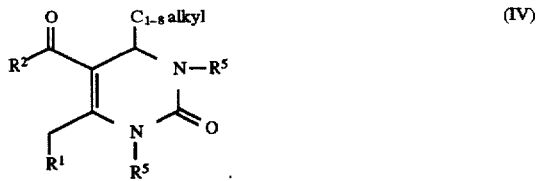

Additionally, N-substituted ureas and O-substituted ureas (e.g., O-methylisourea) can be utilized in place of urea (C") to afford the corresponding N-substituted dihydropyrimidinones. A number of N-substituted ureas are commercially available and/or could be easily prepared by one of ordinary skill in the art.

The ratio of starting materials is preferably 1:1:1.5 of A:B:C; however, varying the ratio (e.g., 2:1:3, 1:1:3 or 2:1:1.5 of A:B:C) also gave higher yields than the prior art methods (e.g., Folkers method).

The reaction of β-keto ester or diketone (A), aldehyde or ketone (B) and urea (C) in one pot with an unprecedented combination of a boron reagent, a metal salt and a catalyst affords 5-(alkyl or alkoxy)carbonyl-6-alkyl-4-(aryl or alkyl)-3,4-2(1H)-dihydropyrimidinone (I) in higher yields than obtained by known methods. The boron reagent used in the instant invention is $BF_3$ which is commercially available in a variety of forms, all of which can be used in the method of the instant invention. More specifically, the boron reagent is selected from $BF_3$, $BF_3 \cdot 2H_2O$, $BF_3 \cdot Me_2S$, $BF_3 \cdot HOAc$, $BF_3 \cdot R_2O$ (e.g., $BF_3 \cdot Et_2O$, $BF_3 \cdot Me_2O$, $BF_3$-tert-butyl methyl etherate), $BF_3 \cdot ROH$ (e.g., $BF_3 \cdot CH_3OH$, $BF_3 \cdot CH_3CH_2CH_2OH$). Preferably, the boron reagent is $BF_3 \cdot Et_2O$.

A variety of metal salts can be utilized in the novel reaction of the present invention. For example, copper (I) chloride, copper (I) oxide, copper (II) chloride, copper (II) sulfate, copper (II) acetate, nickel (II) bromide, palladium (II) acetate, copper bromide or palladium acetoacetate can all be used as the metal salt. Preferably, the metal salt is copper (I) chloride, copper (I) oxide, copper (II) chloride, copper (II) sulfate, copper (II) acetate, nickel (II) bromide or palladium (II) acetate. More preferably, the metal salt is copper (I) oxide, copper (I) chloride, nickel (I) bromide or palladium (II) acetate. Most preferably, the metal salt used in the reaction is copper (I) oxide. Catalytic amounts of the metal salt are preferable to one full equivalent in the instant reaction.

The catalyst used in the instant reaction can be a number of different Bronsted acids or bases or an alcohol. For example, suitable catalysts include, but are not limited to, acetic acid, trifluoroacetic acid, methanol, sulfuric acid, MsOH, dichloroacetic acid, $HBr \cdot PPh_3$, $NH_4OAc$, triethylamine, pyridine, cinchonine, quinine or quinidine. Preferably, the catalyst is selected from acetic acid, trifluoroacetic acid, methanol, sulfuric acid, MsOH, dichloroacetic acid, $HBr \cdot PPh_3$ or $NH_4OAc$. More preferably, the catalyst is selected from acetic acid, trifluoroacetic acid or methanol. Most preferably, acetic acid is used as the catalyst.

The reaction can be ran at a temperature range of about 40° C. to about 100° C. Preferably, the temperature is about 65° C. The reaction mixture is heated for a period of 1 to 20 hours depending on the starting materials used. Preferably, the reaction mixture is heated for a period of 6 to 20 hours; most preferably, for about 18 hours.

In a particularly preferred embodiment of the instant invention, 1 eq. of β-keto ester (A), 1 eq. of arylaldehyde (B), 1.5 eq. urea (C) are reacted in the presence of 1.3 eq. $BF_3 \cdot Et_2O$, 10 mol % $Cu_2O$, and 10 mol % AcOH in THF at 65° C. for 18 h to afford the dihydropyrimidinone (I) in high yield.

Abbreviations used in the instant specification are as follows:
AcOH or HOAc=acetic acid
DMSO=dimethyl sulfoxide
Et=ethyl
EtOAc=ethyl acetate
EtOH=ethanol
eq.=equivalent
Me=methyl
MeOH=methanol
MsOH=methanesulfonic acid
$NH_4OAc$=ammonium acetate
Ph=phenyl
THF tetrahydrofuran The term "alkyl," as used herein, includes both straight and branched chain alkanes of the number of carbon atoms specified (e.g., $C_{1-10}$ alkyl), or any number within this range (i.e., methyl, ethyl, 1-propyl, 2-propyl, n-butyl, s-butyl, t-butyl, etc.).

The term "halogenated alkyl," as used herein, includes both straight and branched chain alkanes of the number of carbon atoms specified (e.g., halogenated $C_{1-10}$ alkyl), or any number within this range, wherein one or more of the hydrogen atoms on the alkyl chain is replaced with a halogen atom (e.g., CF$_3$).

The term "alkoxy," as used herein, refers to straight or branched chain alkoxides of the number of carbon atoms specified (e.g., C$_{1-6}$ alkoxy), or any number within this range (i.e., methoxy, ethoxy, etc.).

The term "halogenated alkoxy," as used herein, includes both straight and branched chain alkoxides of the number of carbon atoms specified (e.g., halogenated C$_{1-6}$ alkoxy), or any number within this range, wherein one or more of the hydrogen atoms is replaced with a halogen atom (e.g., OCF$_3$).

The term "aryl," as used herein, refers to unsubstituted, mono-, di-, tri- or tetra- or penta-substituted aromatic groups such as phenyl or naphthyl. Preferably, the aryl group is unsubstituted, mono-, di- or tri-substituted. Examples of substituents which can be present on the phenyl or naphthyl group include, but are not limited to, halogen, C$_{1-6}$ alkyl, C$_{1-6}$ alkoxy, halogenated C$_{1-6}$ alkyl or halogenated C$_{1-6}$ alkoxy.

As used herein, the term "halogen" shall include, iodine, bromine, chlorine and fluorine.

The following examples are provided to further define the invention without, however, limiting the invention to the particulars of these examples.

EXAMPLE 1

5-Methoxycarbonyl-6-methyl-4-phenyl-3,4-dihydropyrimidin-2(1H)-one

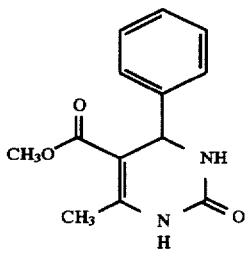

To a dry round bottom flask containing methyl acetonacetate (0.2322 g, 2.0 mmol), benzaldehyde ( 0.2122 g, 2.0 mmol) and urea (0.18 g, 3.0 mmol) in 3.6 ml of dry THF (0.5M) was added AcOH (10 mol %), CuCl (10 mol %) and 1.3 equivalent of BF$_3$·Et$_2$O (2.6 mmol). The reaction was heated at 65° C. for 18 h. The reaction was quenched with one volume equivalent of 10% Na$_2$CO$_3$ solution and diluted with EtOAc (one volume equivalent). The organic layer containing the product was turned over to toluene and the title compound was crystallized in 88% yield; mp 204°–208° C.

1H NMR (250 MHz, CDCl$_3$)δ 8.08 (s, 1H), 7.30 (M, 5H), 5.70 (s, 1H), 5.39 (d, 1H), 3.62 (s, 3H), 2.34 (s, 3H).

EXAMPLE 2

4-(3,4-Difluorophenyl)-6-ethyl-5-methoxycarbonyl-3,4-dihydropyrimidin-2(1H)-one

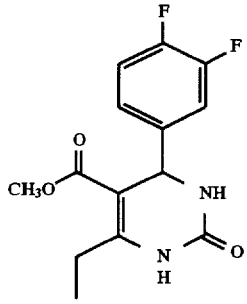

To a dry round bottom flask containing methyl propionylacetate (2.0 g, 15.4mmol), 3,4-difluorobenzaldehyde (2.1885 g, 15.4 mmol), and urea (1.39 g, 23.1 mmol) in 28 ml of dry THF (0.5M) was added AcOH (10 mol %), Cu$_2$O (10 mol %) and 1.3 equivalent of BF$_3$·OEt$_2$ (20.0 mmol). The reaction was heated at 65° C. for 18 h. Then, the reaction mixture was quenched with one volume equivalent of 10% Na$_2$CO$_3$ and diluted with one volume equivalent of EtOAc. The organic layer containing the product was turned over to toluene and the title compound was crystallized in 90% yield; mp 180°–184° C.

NMR $^1$H (250 MHz, DMSO-d$_6$)δ 9.31 (s, 1H), 7.80 (s, 1H), 7.40 (m, 1H), 7.20 (m, 1H), 7.06 (m, 1H), 5.14 (d, 1H), 3.54 (s, 3H), 2.65 (m, 2H), 1.11 (t, 3H).

EXAMPLE 3

5-Methoxycarbonyl-6-methoxymethyl-4-(3 4-difluorophenyl)-3,4-dihydropyrimidin-2(1H)-one

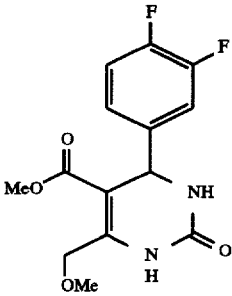

To a dry round bottom flask containing methoxy acetoacetate (2.0 g, 13.7 mmol), 3,4-difluorobenzaldehyde ( 1.95 g, 13.7 mmol) and urea ( 1.23 g, 20.6 mmol) in 28 ml of dry THF (0.5M) was added AcOH (10 mol %), CuCl (10 mol %) or Cu(OAC)$_2$ and 1.3 e.g. of BF$_3$·Et$_2$O (2.6 mmol). The reaction was heated at 65° C. for up to 18 h. The reaction was quenched with one volume equivalent of 10% Na$_2$CO$_3$ solution and diluted with EtOAc (one volume equivalent). The organic layer containing the product was turned over to toluene and the title compound was crystallized in 90% yield; mp: 116°–120° C.

$^1$H NMR (250 MHz, CDCl$_3$)δ 7.70 (br s, 1H), 7.06 (m, 3H), 6.91 (br s, 1H), 5.32 (s, 1H), 4.62 (s, 2H), 3.63 (s, 3H), 3.44 (s, 3H).

The compounds shown below in Table 1 can be readily prepared by one of ordinary skill in the art according to the methods described in the above Examples by using readily available starting materials.

TABLE I

| Chemical Name | Structure |
|---|---|
| 6-ethyl-5-methoxycarbonyl-4-phenyl-3,4-2(1H)-dihydropyrimidinone | 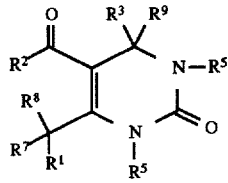 |
| 6-ethyl-5-methoxycarbonyl-4-(4-methoxyphenyl)-3,4-2(1H)-dihydropyrimidinone | |
| 4-(4-chlorophenyl)-6-ethyl-5-methoxycarbonyl-3,4-2(1H)-dihydropyrimidinone | 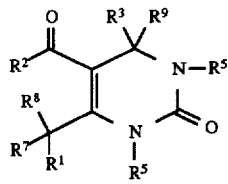 |
| 6-ethyl-5-methoxycarbonyl-4-(4-nitrophenyl)-3,4-2(1H)-dihydropyrimidinone | |

While the foregoing specification teaches the principles of the present invention, with examples for the purpose of illustration, it will be understood that the practice of the invention encompasses all of the usual variations, adaptations and/or modifications as come within the scope of the following claims and their equivalents.

What is claimed is:
1. A method of forming a compound of formula I

(I)

comprising reacting

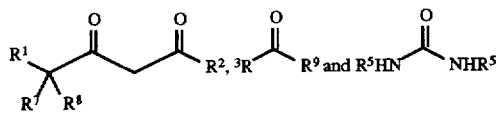

in the presence of a boron reagent, a metal salt and a catalyst to form the compound (I)

(I)

wherein
the boron reagent is selected from $BF_3$, $BF_3 \cdot 2H_2O$, $BF_3 \cdot Me_2S$, $BF_3 \cdot HOAc$, $BF_3 \cdot R_2O$ (e.g., $BF_3 \cdot Et_2O$, $BF_3 \cdot Me_2O$, $BF_3$-tert-butyl methyl etherate), $BF_3 \cdot ROH$ (e.g., $BF_3 \cdot CH_3OH$, $BF_3 \cdot CH_3CH_2CH_3OH$); the metal salt is selected from copper (I) chloride copper (I) oxide copper (II) chloride, copper (H) sulfate copper (H) acetate, nickel (H) bromide, palladium (II) acetate, copper bromide or palladium acetoacetate;
the catalyst is selected from acetic acid, trifluoroacetic acid, methanol, sulfuric acid, MsOH, dichloroacetic acid, $HBr \cdot PPh_3$, $NH_4OAc$, triethylamine, pyridine, cinchonine, quinine or quinidine;
$R^1$, $R^7$ and $R^8$ are each independently selected from hydrogen, halogen, halogenated $C_{1-10}$ alkyl, unsubsituted or substituted aryl, or unsubstituted or substituted $C_{1-10}$ alkyl wherein the substituent on the alkyl is selected from $C_{1-6}$ alkoxy, halogenated $C_{1-6}$ alkoxy or aryl;
$R^2$ is $C_{1-10}$ alkyl, $OR^6$, unsubstituted $C_{3-6}$ cycloalkyl or mono-, di- or tri-substituted $C_{3-6}$ cycloalkyl wherein the substitutents on the cycloalkyl are independently selected from hydroxy, $C_{1-6}$ alkyl, halogenated $C_{1-6}$ alkyl, $C_{1-6}$ alkoxy or halogenated $C_{1-6}$ alkoxy;
$R^3$ and $R^9$ are each independently selected from hydrogen, $C_{1-10}$ alkyl or

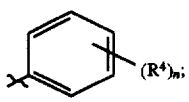

each $R^4$ is independently selected from hydrogen, halogen, cyano, $C_{1-6}$ alkoxy, halogenated $C_{1-6}$ alkoxy, nitro, $C_{1-10}$ alkyl or halogenated $C_{1-10}$ alkyl;
each $R^5$ is independently selected from hydrogen or $C_{1-10}$ alkyl;
$R^6$ is selected from unsubstituted or substituted $C_{1-10}$ alkyl wherein the substituent on the alkyl is selected from $C_{1-6}$ alkoxy, halogenated $C_{1-6}$ alkoxy or aryl; unsubstituted $C_{3-6}$ cycloalkyl or mono-, di- or tri-substituted $C_{3-6}$ cycloalkyl wherein the substitutents on the cycloalkyl are independently selected from hydroxy, $C_{1-6}$ alkyl, halogenated $C_{1-6}$ alkyl, $C_{1-6}$ alkoxy or halogenated $C_{1-6}$ alkoxy; or unsubstituted or substituted aryl; and n is an integer from one to five.

2. The method of claim 1, wherein the metal salt is selected from copper (I) chloride, copper (I) oxide, copper (II) chloride, copper (II) sulfate, copper (II) acetate, nickel (II) bromide or palladium (II) acetate;

the catalyst is selected from acetic acid, trifluoroacetic acid, methanol, sulfuric acid, MsOH, dichloroacetic acid, HBr·PPh$_3$ or NH$_4$OAc;

$R^1$ is selected from hydrogen or $C_{1-8}$ alkyl;

$R^2$ is $C_{1-8}$ alkyl or $OR^6$;

$R^3$ is selected from $C_{1-8}$ alkyl or

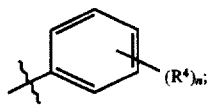

each $R^4$ is independently selected from hydrogen, halogen, $C_{1-5}$ alkoxy, nitro, $C_{1-8}$ alkyl or halogenated $C_{1-8}$ alkyl;

each $R^5$ is independently selected from hydrogen or $C_{1-8}$ alkyl;

$R^6$ is $C_{1-8}$ alkyl;

$R^7$, $R^8$ and $R^9$ are hydrogen; and n is an integer from one to three.

3. The method of claim 1, further comprising the step of isolating the compound I

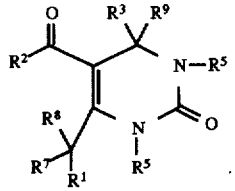
(I)

4. The method of claim 3, comprising reacting

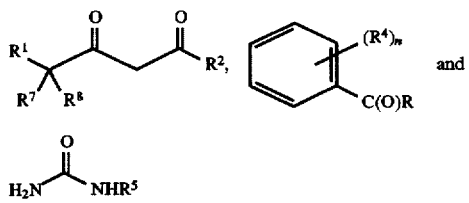

in the presence of a boron reagent, a metal salt and a catalyst to form the compound (II)

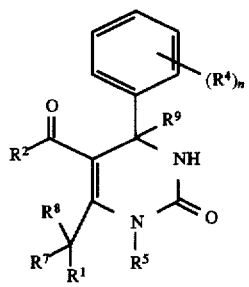
(II)

wherein the boron reagent is selected from BF$_3$, BF$_3$·2H$_2$O, BF$_3$·Me$_2$S, BF$_3$·HOAc, BF$_3$·R$_2$O (e.g., BF$_3$·Et$_2$O, BF$_3$·Me$_2$O, BF$_3$·tert-butyl methyl etherate), BF$_3$·ROH (e.g., BF$_3$·CH$_3$OH, BF$_3$·CH$_3$CH$_2$CH$_2$OH);

the metal salt is selected from copper (I) chloride, copper (I) oxide, copper (II) chloride, copper (II) sulfate, copper (II) acetate, nickel (II) bromide, palladium (II) acetate, copper bromide or palladium acetoacetate;

the catalyst is selected from acetic acid, trifluoroacetic acid, methanol, sulfuric acid, MsOH, dichloroacetic acid, HBr·PPh$_3$, NH$_4$OAc, triethylamine, pyridine, cinchonine, quinine or quinidine.

5. The method of claim 4, comprising reacting

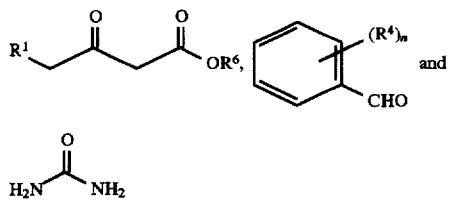

in the presence of a boron reagent, a metal salt and a catalyst to form the compound (III)

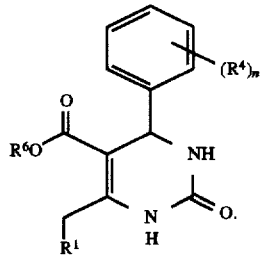

6. The method of claim 1, wherein the reaction is carried out in one pot.

7. The method of claim 1, wherein the reaction is run in a solvent selected from an ether, an alcohol, a halogenated hydrocarbon or an acid.

8. The method of claim 7, wherein the solvent is selected from tetrahydrofuran, methanol, methylene chloride or acetic acid.

9. The method of claim 8, wherein the solvent is tetrahydrofuran.

10. The method of claim 7, wherein the boron reagent is selected from BF$_3$, BF$_3$·2H$_2$O, BF$_3$·Me$_2$S, BF$_3$·HOAc, BF$_3$·Et$_2$O, BF$_3$·Me$_2$O, BF$_3$·t-BuOMe, BF$_3$·CH$_3$OH or BF$_3$·CH$_3$CH$_2$CH$_2$OH.

11. The method of claim 10, wherein the boron reagent is BF$_3$·Et$_2$O.

12. The method of claim 10, wherein the metal salt is selected from copper (I) chloride, copper (I) oxide, copper (II) chloride, copper (II) sulfate, copper (II) acetate, nickel (II) bromide, palladium (II) acetate, copper bromide or palladium acetoacetate.

13. The method of claim 12, wherein the metal salt is selected from copper (I) oxide, copper (I) chloride, nickel (II) bromide or palladium (II) acetate.

14. The method of claim 13, wherein the metal salt is copper (I) oxide.

15. The method of claim 12, wherein the catalyst is selected from acetic acid, trifluoroacetic acid, methanol, sulfuric acid, MsOH, dichloroacetic acid, HBr·PPh$_3$, NH$_4$OAc, triethylamine, pyridine, cinchonine, quinine or quinidine.

16. The method of claim 15, wherein the catalyst is selected from acetic acid, trifluoroacetic acid or methanol.

17. The method of claim 16, wherein the catalyst is acetic acid.

18. The method of claim 11, wherein the metal salt is selected from copper (I) oxide, copper (I) chloride, nickel (II) bromide or palladium (II) acetate; the catalyst is selected from acetic acid, trifluoroacetic acid or methanol; and the solvent is selected from tetrahydrofuran, methanol or methylene chloride.

19. The method of claim 18, wherein the metal salt is copper (I) oxide, the catalyst is acetic acid and the solvent is tetrahydrofaran.

20. The method of claim 19, wherein the reaction is carried out in one pot.

21. The method of claim 20, wherein the reaction is run at a temperature range of about 40° C. to 100° C.

22. The method of claim 21, wherein the reaction is run at a temperature of about 65° C.

23. The method of claim 21, wherein the reaction is heated for a period of from 1 to 20 hours.

24. The method of claim 23, wherein the reaction is heated for about 18 hours.

* * * * *